United States Patent [19]

Botta et al.

[11] 4,104,194
[45] Aug. 1, 1978

[54] METHOD FOR PROTECTING METAL FROM EROSION

[75] Inventors: Artur Botta, Krefeld; Christian Rasp, Cologne, both of Germany

[73] Assignee: Bayer Aktiengesellschaft, Leverkusen, Germany

[21] Appl. No.: 797,651

[22] Filed: May 16, 1977

Related U.S. Application Data

[62] Division of Ser. No. 591,789, Jun. 30, 1975, Pat. No. 4,048,174.

[30] Foreign Application Priority Data

Jul. 23, 1974 [DE] Fed. Rep. of Germany ....... 2435406

[51] Int. Cl.² .............................................. C09K 3/00
[52] U.S. Cl. ................................. 252/390; 21/2.7 R; 21/2.5 R; 252/392
[58] Field of Search .............. 252/392, 390; 21/2.5 R, 21/2.7 R; 260/309.2, 296 H, 283 SY, 251 A

[56] References Cited

U.S. PATENT DOCUMENTS

| | | | |
|---|---|---|---|
| 3,117,970 | 1/1964 | Weisbach | 260/283 SY |
| 3,189,616 | 6/1965 | Loffler et al. | 260/309.2 |
| 3,920,678 | 11/1975 | Butula | 252/390 X |
| 3,987,054 | 10/1976 | Butula | 252/390 X |

*Primary Examiner*—Benjamin R. Padgett
*Assistant Examiner*—Josephine L. Barr
*Attorney, Agent, or Firm*—Burgess, Dinklage & Sprung

[57] ABSTRACT

1,2-Fused five-membered or six-membered 1,3-dinitrogen-heterocyclic compounds, useful as anti-corrosion agents, having the formula

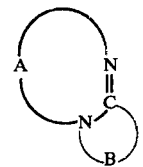

(I)

wherein
A is an optionally substituted, optionally polynuclear orth- or peri-arylene radical and
B is an optionally substituted alkylene chain

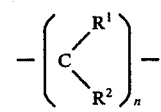

wherein
$R^1$ and $R^2$ individually represent hydrogen and/or optionally substituted aliphatic, cycloaliphatic, araliphatic or aromatic radicals and
$n$ represents a number from 3 to 6, or
B is an optionally substituted 1,8-naphthylene, 2,2'-diphenylene or 4,5-phenanthrylene radical, are prepared by splitting a five-membered or six-membered 1,3-dinitrogen-heterocyclic compound, which contains a 2-(ω-amino group) side chain, having the formula

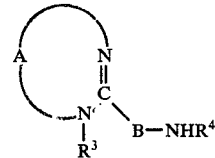

(II)

wherein
A and B have the meanings indicated above and
$R^3$ and $R^4$ are hydrogen, lower alkyl, cycloalkyl or aralkyl but at least one of the two radicals $R^3$ and $R^4$ must represent hydrogen.

8 Claims, No Drawings

METHOD FOR PROTECTING METAL FROM EROSION

This is a division, of application Ser. No. 591,789, filed June 30, 1975 now U.S. Pat. No. 4,048,174 Sept. 13, 1977.

BACKGROUND

This invention relates to a process for the preparation of 1,2-fused five-membered or six-membered 1,3-dinitrogen-heterocyclic compounds and their use as anticorrosion agents. The compounds, some of which are known, have the general formula

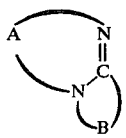

wherein
A denotes an optionally substituted, optionally polynuclear ortho- or peri-arylene radical and B denotes an optionally substituted alkylene chain

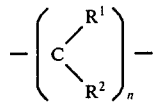

in which
$R^1$ and $R^2$ individually represent hydrogen and/or optionally substituted aliphatic, cycloaliphatic, araliphatic or aromatic radicals and
$n$ represents an integer from 3 to 6, especially 3 to 5, or
B denotes an optionally substituted 1,8-naphthylene, 2,2'-diphenylene or 4,5-phenanthrylene radical. Some compounds of this nature have already been disclosed. In particular, these are compounds of the formula I, in which
B denotes an aliphatic hydrocarbon chain $-(CH_2)_n-$.

It is known to prepare these compounds by starting from o-nitrochlorobenzenes and alkyleneimines, which are condensed to N-[o-nitrophenyl]-alkyleneimines. These are converted to the 1,2-alkylenebenzimidazoles: [J. Chem. Soc. 3275 (1955); J. Chem. Soc. 1666–1669 (1963)] either directly by reduction with $TiCl_3$ in concentrated hydrochloric acid [Tetrahedron (London) 24 (1968) 12, 4581-8] or by catalytic reduction followed by oxidation with Caro's acid [Ber. 41, 682 (1908)] or with peroxytrifluoroacetic acid [J. Am. Chem. Soc. 83, 3518 (1961)] or by diazotisation and thermal decomposition of the axide, obtainable by a Sandmeyer reaction, in nitrobenzene at 170° C. Furthermore, 1,2-tetramethylenebenzimidazole has been obtained in only 16% yield by condensation of nitrobenzene with N-lithium-piperidine [Ann. 594, 159 (1955)]. Finally, some 1,2-alkylenebenzimidazoles have been prepared by cyclising condensation of o-phenylenediamine with ω-halogenocarboxylic acid iminoether hydrochlorides [J. Org. Chem. 27, 2165 (1962)].

However, probably none of these proposed methods deserves consideration as the basis of an industrially economical process, since on the one hand they comprise expensive process steps and on the other they only give low yields.

SUMMARY

According to the present invention, 1,2-fused five-membered or six-membered 1,3-dinitrogen-heterocyclic compounds of the formula

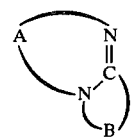

wherein
A denotes an optionally substituted, optionally polynuclear ortho- or peri-arylene radical and
B denotes an optionally substituted alkylene chain

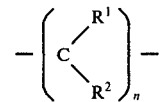

in which
$R^1$ and $R^2$ in particular represent hydrogen and/or optionally substituted aliphatic, cycloaliphatic, araliphatic or aromatic radicals and
$n$ represents a number from 3 to 6, especially 3 to 5, or
B denotes an optionally substituted 1,8-naphthylene, 2,2'-diphenylene or 4,5-phenanthrylene radical,
are prepared by a method wherein five-membered and six-membered 1,3-dinitrogen-heterocyclic compounds, which contain 2-(ω-amino group) side chains, of the general formula

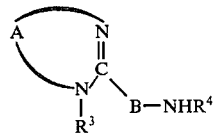

in which
A and B have the range of meanings indicated above and $R^3$ and $R^4$ represent hydrogen, lower alkyl, cycloalkyl or aralkyl but at least one of the two radicals $R^3$ and $R^4$ must represent hydrogen
are split at temperatures of 150° to 400° C, preferably in the presence of acids or acid catalysts.

The reaction is new and was not to be expected from the state of the art.

DESCRIPTION

The range of meanings of the abovementioned radicals A, B, $R^1$, $R^2$, $R^3$ and $R^4$ is explained in more detail below:

Examples of possible optionally substituted 1,2- or o-arylene radicals are the 1,2-phenylene, 1,2- and 2,3-naphthylene, 1,2- and 2,3-anthracylene, 1,2-, 2,3-, 3,4- and 9,10-phenanthrylene, 2,3- and 3,4-pyridylene and quinolinylene radical, preferably the 2,3- and 3,4-pyridylene radical, the naphthylene radical and the phenylene radical, especially the phenylene radical.

Examples of possible optionally substituted polynuclear 1,8- or peri-arylene radicals are the 1,8-naphthylene, 1,9-anthracylene, 1,10-phenanthrylene and 4,5-quinolinylene radical, especially the 1,8-naphthylene radical.

Examples of possible optionally substituted 2,4-diphenylene radicals are the 2,2'-diphenylene, 4,5-phenanthrylene, 4,5-fluorenylene and 4,5-carbasolylene radical, especially the 2,2'-diphenylene radical.

Examples of possible aliphatic radicals $R^1$, $R^2$, $R^3$ and $R^4$ are straight-chain or branched radicals with up to 12, preferably up to 6, and especially up to 4, C atoms.

Examples of possible cycloaliphatic radicals $R^1$, $R^2$, $R^3$ and $R^4$ are those with up to 8 C atoms, preferably cyclopentyl and cyclohexyl.

Examples of possible araliphatic radicals $R^1$, $R^2$, $R^3$ and $R^4$ are those with 7 to 12 C atoms, preferably 7 to 9 C atoms, especially the benzyl radical.

Examples of possible optionally substituted aromatic radicals $R^1$ and $R^2$ are those with 6 to 14 C atoms, preferably the naphthyl and phenyl radical, especially the phenyl radical. Where the abovementioned radicals A, B, $R^1$ and $R^2$ are monovalent and divalent aromatic radicals, these may be substituted, for example by halogen (fluorine, chlorine, bromine and iodine), preferably chlorine and bromine, the $CF_3$— group, an alkoxy or aryloxy group, a dialkylamino group or, especially, lower alkyl.

Compounds which can be obtained preferentially in accordance with the process of the invention are those of the formula

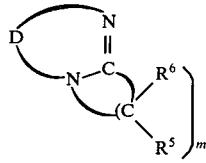

in which

D denotes a 2,3- or 3,4-pyridylene radical, a 1,2-, 2,3- or 1,8-naphthylene radical or 1,2-phenylene radical, these radicals being optionally substituted, preferably by alkyl with up to 6 C atoms, $R^5$ and $R^6$ represent hydrogen or alkyl with up to 6 carbon atoms, cyclopentyl, cyclohexyl, benzyl or phenyl and $m$ denotes one of the numbers 3, 4, 5 or 6, the $m$ radicals $R^5$ and $m$ radicals $R^6$ optionally being different.

Especially, compounds which can be obtained preferentially in accordance with the process of the invention are those of the formula

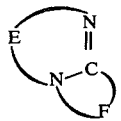

wherein

E denoted a substituted or unsubstituted radical selected from the group of 1,2-phenylene, 1,2-naphthylene and 2,3-pyridylene and F denotes a substituted or unsubstituted radical selected from the group of trimethylene, pentamethylene, 2,2'-diphenylene and 1,8-naphthylene.

The starting materials for the process according to the invention are known and/or can be prepared according to known processes, for example according to German Patent 1,131,688, British Patent 1,023,793, German Published Specification 2,110,227 or German Published Specification 2,321,054.

Any desired 5-membered or 6-membered polynuclear 2-(ω-amino-substituted) 1,3-dinitrogen-heterocyclic compounds of the formula II can be used for the process according to the invention, for example 2-(3'-aminopropyl)-, 2-(3'-amino-1'-methylpropyl)-, 2-(3'-amino-1',2'-dimethyl-propyl)-, 2-(3'-amino-3',3'-dimethylpropyl)-, 2-(3'-amino-3'-ethyl-propyl)-, 2-(3'-amino-3'-benzyl-propyl)-, 2-(4'-aminobutyl)-, 2-(4'-amino-1'-methyl-butyl)-, 2-(4'-amino-3'-butyl-butyl)-, 2-(4'-amino-2',3'-dimethyl-butyl)-, 2-(4'-amino-4',4'-dimethyl-butyl)-, 2-(4'-amino-4'-phenyl-butyl)-, 2-(5'-aminopentyl)-, 2-(5'-amino-1'-bis 5'-methyl-pentyl)-, 2-(5'-amino-1'-bis 5'-ethylpentyl)-, 2-(5'-amino-1'-bis 5'-propylpentyl)-, 2-(5'-amino-1'-bis 5'-isopropyl-pentyl)-, 2-(5'-amino-1'-bis 5'-butylpentyl)-, 2-(5'-amino-1'-bis 5'-isobutyl-pentyl)-, 2-(5'-amino-1'-bis 5'-tert.-butylpentyl)-, 2-(5'-amino-1'-bis 5'-cyclohexyl-pentyl)-, 2-(5'-amino-1'-bis 5'-benzyl-pentyl)-, 2-(5'-amino-1'-bis 5'-phenyl-pentyl)-, 2-(5'-amino-1',3'-dimethyl-pentyl)-, 2-(5'-amino-2'-ethyl-3'-p-chlorophenyl-pentyl)-, 2-(5'-amino-4'-m-methoxyphenyl-pentyl)-, 2-(5'-amino-2'-m-trifluoromethyl-phenyl-pentyl)-, 2-(5'-amino-3'-p-tolyl-pentyl)-, 2-(6'-aminohexyl)-, 2-(3'-methyl-aminopropyl)-, 2-(4'-ethylaminobutyl)-, 2-(3'-tert.-butylaminopropyl)-, 2-(5'-cyclohexylaminopentyl)-, 2-(5'-benzylaminopentyl)-, 2-(5'-phenethylaminopentyl)-, 2-(o-aminobenzyl)-, 2-(o-methylamino-α,α-dimethyl-benzyl)-, 2-(o-amino-p-dimethyl-amino-benzyl)-, 2-(o-aminomethylphenyl)-, 2-(o-propylamino-methylphenyl)-, 2-(o-amino-phenethyl)-, 2-(o-isopropylamino-p-bromo-phenethyl)-, 2-(o-amino-hexahydro-phenethyl)-, 2-[o-(2'-aminoethyl)-phenyl]-, 2-[o-(2'-methyl-aminoethyl)-p-fluorophenyl]-, 2-(o-aminomethyl-phenethyl)-, 2-[8'-amino-naphthyl-(1')]-, 2-[8'-ethylamino-5'-bromo-napthyl-(1')]-, 2-[2''-amino-diphenylyl-(2')]-, 2-[2''-amino-4''-ethoxy-diphenylyl-(2')]-, 2-[5'-amino-phenanthryl-(4')]- and 2-[5'-benzylaminophenanthryl-(4')]-benzimidazole, -4-methyl-benzimidazole, -5-methyl-benzimidazole, -5-fluorobenzimidazole, -5-chloro-benzimidazole, -5-methoxybenzimidazole, -5-phenoxybenzimidazole, -5-trifluoromethylbenzimidazole, -4,6-dimethylbenzimidazole, -5-tert.butylbenzimidazole, -6-benzylbenzimidazole, -naphtho-(1,2)-imidazole, -naphtho-(2,3)-imidazole, -anthracen-(1,2)-imidazole, -anthracen-(2,3)-imidazole, -phenanthren-(9,10)imidazole, -pyrido-(2,3)-imidazole, -pyrido-(3,4)-imidazole, -quinolino-(2,3)-imidazole, -quinolino-(6,7)-imidazole, -perimidine, -benzperimidine and -azaperimidine and, where the abovementioned 2-(ω'-amino)-side chains contain a primary amino group, also -1-methyl-benzimidazole, -1-ethylbenzimidazole, 1-tert.butyl-benzimidazole, -1-cyclohexylbenzimidazole, -1,4-dimethylbenzimidazole, -1-benzyl-5-methylbenzimidazole, -1-phenethyl-5-trifluoromethylbenzimidazole, -1-ethyl-naphthimidazole, -1-sec.butyl-perimidine and -1-benzyl-benzperimidine.

Though the process according to the invention can optionally also be carried out without addition of a catalyst, it is advantageous to carry out the thermal decomposition in the presence of acids or acid catalysts.

Any desired acids can be used as the acid for the process according to the invention. For example it is possible to use mineral acids, such as hydrogen halide acids, especially hydrochloric acid and hydrobromic acid, sulphuric acid, bisulphates, especially of the alkali metals, phosphoric acid, polyphosphoric acids, boric acid and tetrafluoboric acid, aliphatic and aromatic sulphonic acids such as methanesulphonic acid, hexanesulphonic acid, dodecanesulphonic acid, cyclohexanesulphonic acid, benzenesulphonic acid, toluenesulphonic acid, parachlorobenzenesulphonic acid, benzene-1,3-disulphonic acid, naphthalenesulphonic acid and naphthalenedisulphonic acids, and aliphatic and aromatic phosphonic acids and phosphinic acids such as cyclohexylphosphonic acid, phenylphosphonic acid and dimethylphosphinic acid.

Equally it is also possible to use Lewis acids, for example zinc-(II) chloride, tin-(II) chloride and boron trifluoride, aluminium chloride and titanium tetrachloride.

As acid catalysts it is possible to use acidactivated siliceous earths and bleaching earths such as montmorillonite, silicoaluminates and silica gel, siliceous earths being understood as finely divided materials which contain silica and/or aluminium oxide. Such siliceous earths and bleaching earths can be activated by acid treatment in a manner which is in itself known (Chemie für Labor und Betrieb, 1956, page 422; Ullmann, 3rd edition, volume 9, page 271 et seq.; volume 8, page 801 to 804), and for this purpose mineral acids such as sulphuric acid, phosphoric acid, hydrochloric acid, perchloric acid or hydrofluoric acid can be used.

Equally, natural or synthetic acid ion exchangers such as zeolites or exchanger resins can be used, exchanger resins being understood as insoluble resins which consist of inert 2-dimensionally or 3-dimensionally crosslinked polymers which are substituted by reactive groups such as phosphoric, phosphonic, sulphuric or sulphonic acid groups.

In particular it is possible to use resins which contain one sulphonic acid group per 0.5 to 2 monomer units of the resin (Ullmann, 3rd edition, volume 8, page 806 to 822, especially page 816; German Patent 915,267).

Equally it is possible to use acid-activated molecular sieves; it is also possible to use mixtures of the abovementioned acids and/or acid-activated siliceous earths and bleaching earths and/or acid ion exchangers.

The amount of acid or acid catalyst which is used in the process according to the invention can be varied within a very wide range. In general, 0.0001-times to twice the equivalent amount of acid is employed per mol of the compound of the formula II, but larger excesses are also not critical.

It is possible to use either catalytic or stoichiometric amounts of acid.

If only catalytic amounts of acid are used, these can in general be about 0.0001 to about 0.2, especially about 0.01 to about 0.1, acid equivalent per mol of the starting compound of the formula II which is employed.

If the process according to the invention is carried out with approximately stoichiometric amounts of acid, it is possible to use about 0.8 to about 2.5, especially about 1 to about 2, acid equivalents per mol of starting compound of the general formula II. It is advantageous to use approximately stoichiometric amounts of acids if, for example, it is desired to obtain a salt or an acid addition compound of the process product of the general formula I as the process product.

The amount of acid catalyst is in general between about 0.1 to about 200% by weight, preferably between approx. 1 and 25% by weight, relative to the starting compound of the formula II.

The reaction temperatures depend on the reactivity or lability of the starting materials II. In general they lie between 150° and 400° C, preferably between 180° and 350° C and especially between about 200° and 300° C.

The process according to the invention can be carried out either discontinuously (batchwise) or continuously, in the sump phase or in the gas phase. In general, any desired pressure can be chosen; the process can be carried out at normal pressure or under reduced pressure, but also at elevated pressure.

A general embodiment of the process according to the invention is, for example, advantageously to mix the starting compound of the formula II, optionally diluted with an inert solvent, with acid or acid catalysts, bring the mixture to the reaction temperature, if appropriate under the protection of an inert gas, for example nitrogen, and optionally whilst stirring, and heat it to the reaction temperature until the elimination of ammonia or alkylamine or aralkylamine is complete. The thermal elimination of the amine and, if appropriate, its removal from the reaction mixture can be assisted by application of a vacuum or by passing inert gas through the reaction mixture.

In a continuous variant of the process according to the invention, for example, the starting material of the formula II, if appropriate diluted with inert gas or with an inert solvent, is passed as a liquid or gas at the selected reaction temperature over the acid catalyst contained in a fixed bed or fluidised bed.

After completion of the reaction, the reaction mixture is isolated and/or purified in the usual manner, for example by fractional distillation and/or recrystallisation. It can be advantageous, especially if major amounts of acid are used, to neutralise the acid employed before isolating the reaction product. For this purpose, aqueous solutions of the hydroxides, carbonates and bicarbonates of the alkali metals and/or alkaline earth metals can be used in a manner which is in itself known.

An advantageous embodiment of the process according to the invention, using catalytic amounts of acids or acid catalyst, is to use the acid or the acid catalyst repeatedly. To do this, the reaction product is removed after completion of the reaction, for example by distillation, and an appropriate amount of the starting material to be employed is merely added afresh to the distillation residue containing the acid or acid catalyst.

A particularly advantageous embodiment of the process according to the invention is not to employ the starting material of the general formula II as such but to prepare it "in situ" and to convert it, without intermediate isolation, into the desired end product of the general formula I by thermal decomposition, advantageously in the presence of acids or acid catalysts, according to one of the abovementioned embodiments.

For the "in situ" preparation, ortho- or periarylenediamines of the general formula (IV)

are condensed with reactive lactim derivatives (V) or lactam derivatives (VI) of the general formulae

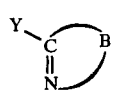 (V) 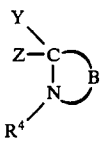

in which

A, B, $R^3$ and $R^4$ have the range of meanings indicated above and

Y — represents halogen, —$OR^5$ or $SR^5$ and

Z — has the same meaning as Y or represents —$OPCl_4$, —$OPOCl_2$, —$OPCl_2$, —$OSO_2Cl$, —$OSO_2R^5$, —OCOCl or —$OCOR^5$ if Y represents halogen, and $R^5$ — represents an alkyl or aryl radical, for example in accordance with the process of German Published Specification 2,110,227, or, especially in accordance with the process of German Published Specification 2,321,054, ortho or peri-arylenediamines of the general formula

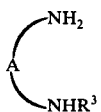 (IV)

are condensed with lactames of the general formula

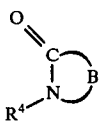 (VII)

in which

A, B, $R^3$ and $R^4$ have the range of meaning above indicated at temperatures of 100° to 300° C, advantageously in presence of acids or acid catalysts.

The process according to the invention will be illustrated for the example of the splitting of 2-(5'-aminopentyl)-benzimidasole by the equation which follows:

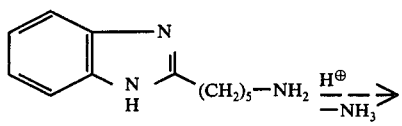

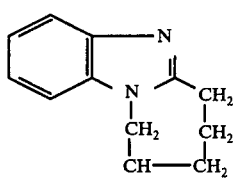

If 2-(5'-methylaminopentyl)-benzimidazole is used as the starting material, the following equation applies:

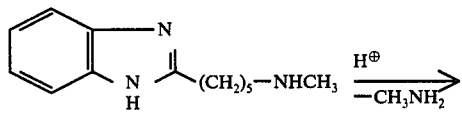

whilst for the thermal splitting of 2-(5'-aminopentyl)-1-ethylbenzimidazole the equation is, analogously:

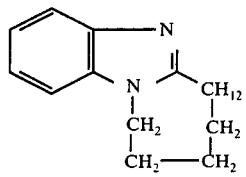

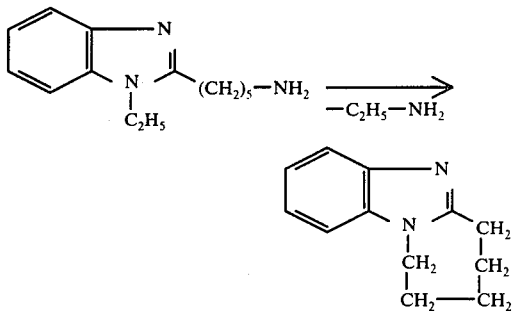

The compounds which can be obtained according to the process of the invention are excellent anti-corrosion agents and anti-corrosion synergistic agents for purely aqueous, aqueous-alcoholic, alcoholic and (mineral) oil systems and for oil-in-water or water-in-oil emulsions; for example, they are used for heat exchangers (cooling or heating circuits), motor oils, drilling and cutting oils, restrainers (pickling inhibitors), oil (petroleum) pipelines and the like (compare Examples 13 - 14). They can be used, for example, in aqueous alcoholic systems in the temperature range of —40° to 120° C and in systems consisting of oils in the temperature range of —40° to 300° C, in concentrations of 1 to 2,000 ppm, preferably of 50 to 300 ppm.

The following Examples illustrate the invention:

EXAMPLE 1

203 g (1 mol) of 2-(5'-aminopentyl)-benzimidazole are fused while stirring. The temperature is brought to 300° C, whereupon ammonia gradually begins to split off, and is kept at 300° - 310° C for 15 hours. The subsequent fractional distillation in vacuo gives, in addition to 75 g (40.3% of theory) of 1,2-pentamethylenebenzimidazole of the following formula, boiling point $_{0.05}$ 145°-148° C and melting point 126° C, 70 g (34.5%) of recovered starting material of boiling point$_{0.05}$ 210°-215° C. 42 g of resinous distillation residue remain in the flask.

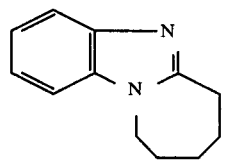

EXAMPLE 2

5 g of methanesulphonic acid are added to 203 g (1 mol) of 2-(5'-aminopentyl)-benzimidazole and the mixture is heated to 300° C over the course of 1 hour, whilst stirring, and is kept at 300° to 320° C for about 10 - 15 hours, until the evolution of $NH_3$ ceases. During the subsequent fractional distillation of the reaction mixture, 159 g (85.4% of theory) of 1,2-pentamethylene-benzimidazole of boiling point $_{0.05}$ 145°–148° C melting point 126° C, as colourless crystals on recrystallisation from 3 parts of ethyl acetate, are obtained.

EXAMPLE 3

74.5 g (0.5 mol) of caprolactam hydrochloride and 60 g (0.55 mol) of o-phenylenediamine are fused under nitrogen, whilst stirring; the elimination of $H_2O$ starts at about 180° C. The temperature of the reaction mixture is gradually raised to 300° C over the course of 5 hours. The melt is then poured into 750 ml of water, the mixture is rendered alkaline with about 75 g of 45% strength NaOH and the organic phase is taken up by extraction by shaking with about 500 ml of $CH_2Cl_2$. After drying over $Na_2SO_4$, the solution is concentrated under reduced pressure and distilled fractionally in an oil pump vacuum. 73.5 g (79% of theory) of 1,2-pentamethylene-benzimidazole are obtained in this way as almost colourless coarse crystals of boiling point$_{0.05}$ 145° C and melting point 126° C on recrystallisation from 3 parts of ethyl acetate.

EXAMPLE 4

A mixture of 57 g (0.5 mol) of caprolactam, 99 g (0.5 mol) of N-benzyl-o-phenylenediamine and 7 g of methanesulphonic acid is heated to 200° C whilst stirring under nitrogen and the temperature is then brought to 250° C over the course of 1½ hours, whilst distilling off the water of condensation through a bridge. The temperature is raised to 320° C over the course of a further 2 hours and is additionally kept at 320° to 340° C for 3 hours, whereupon benzylamine passes over. On subsequent distillation of the residue which remains, 60 g (64.5% of theory) of 1,2-pentamethylenebenzimidazole of boiling point$_{0.05}$ 145° C and melting point 126° C are obtained.

EXAMPLE 5

30 g of catalyst K20 (acid-activated montmorillonite of Messrs. Südchemie, Munich) are added to 176 g (1 mol) of 2-(3'-aminopropyl)-benzimidazole and the mixture is brought to 300° C in 1 hour whilst stirring — the evolution of $NH_3$ starts from 160° C — and is kept at 290° to 310° C for 10 hours. On subsequent distillation under reduced pressure, 120 g (76% of theory) of 1,2-trimethylene-benzimidazole of boiling point$_{0.25}$ 148° – 150° C, and melting point 118° C, on recrystallisation from 3 parts of ethyl acetate, are obtained.

EXAMPLE 6

10 g of metaphosphoric acid are added to 176 g (1 mol) of 2-(3'-aminopropyl)-benzimidazole and the mixture is heated to about 300° C whilst stirring and is kept at this temperature for 12 hours. It is then distilled under reduced pressure and 135 g (85.4% of theory) of 1,2-trimethylenebenzimidazole of boiling point$_{0.2}$ 148° to 150° C and melting point 118° C on recrystallisation from 3 parts of ethyl acetate are obtained.

EXAMPLE 7

A mixture of 128 g (1.5 mols) of pyrrolidone, 180 g (1.66 mols) of o-phenylenediamine and 30 g of 85% strength $H_3PO_4$ is fused whilst stirring the mixture and passing nitrogen over it; from 175° C sump temperature, the elimination of water commences. The mixture is gradually brought to 300° C over the course of 4 hours and is kept at this temperature for 2 hours; in the course thereof, about 45 g of water containing $NH_3$, together with $NH_3$ gas, pass over. The melt is poured into about 2 l of water and rendered alkaline (pH 14) by adding 45% strength sodium hydroxide solution, and the organic phase is taken up by extraction by shaking with 1,000 ml of $CH_2Cl_2$. After concentration under reduced pressure, the residue which remains is distilled and fractionated in an oil pump vacuum, and 176 g (74.1% of theory) of 1,2-trimethylene-benzimidazole of boiling point$_{0.2}$ 144°–146° C and melting point 118° C on recrystallisation from 2 parts of ethyl acetate are obtained.

EXAMPLE 8

75 g (0.75 mol) of N-methylpyrrolidone, 90 g (0.83 mol) of o-phenylenediamine and 15 g of 85% strength $H_3PO_4$ are fused under nitrogen whilst stirring, the elimination of water starting from 180° C. The mixture is gradually heated to 300° C over the course of 8 hours, whereupon not only $H_2O$ but also methylamine passes over from 200° C, and more markedly from 230° C. The melt is additionally kept at 300° C for 2 hours and is then allowed to cool slightly and stirred into a mixture of 100 g of 45% strength NaOH and 1,500 ml of water, and the organic phase is taken up in about 700 ml of $CH_2Cl_2$. On further working up analogously to Example 2c, 85.5 g (72% of theory) of 1,2-trimethylene-benzimidazole (identical with that obtained according to Example 2c) are obtained.

EXAMPLE 9

52 g (0.2 mol) of 2-(5'-amino-3'-tert.-butyl-pentyl)-benzimidazole and 5 g of methanesulphonic acid are fused whilst stirring. Whilst passing nitrogen through the melt, the temperature is brought to 290°–295° C and maintained thereat for 5 hours until the elimination of ammonia has ceased. On subsequent distillation in vacuo, 45 g (97.7% of theory) of 1,2-(3'-tert.-butyl-pentamethylene)-benzimidazole of boiling point$_{0.1}$ 164° C, and melting point 143° C on recrystallisation from 3 parts of ethyl acetate, are obtained.

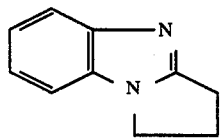

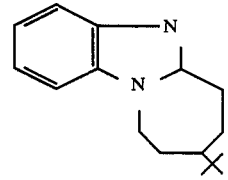

EXAMPLE 10

A mixture of 169 g (1 mol) of 4-tert.-butylcaprolactam, 119 g (1.1 mols) of o-phenylenediamine and 15 g of benzenesulphonic acid is fused under nitrogen, whilst stirring. Over the course of 4 hours at a sump temperature of 200°–230° C, about 18 g of water pass over. The temperature is brought to 315° C over the course of 3 hours whilst passing nitrogen through the melt, and is maintained thereat for a further 2 hours. The melt is then distilled fractionally in vacuo and 221 g (91.2% of theory) of 1,2-(3'-tert.-butyl-pentamethylene)-benzimidazole are obtained; on recrystallisation, colourless crystals of melting point 143° C and boiling point$_{0.1}$ 164° C are obtained.

EXAMPLE 11

A mixture of 79 g (0.5 mol) of 2,3-naphthylenediamine, 42.5 g (0.5 mol) of pyrrolidone and 10 g of 85% strength phosphoric acid is heated under nitrogen whilst stirring; at 200°–220° C, water begins to distil over. The mixture is brought to 280° C over the course of 5 hours and is kept at this temperature for a further 5 hours. On subsequent fractional distillation in vacuo, 65 g (62.5% of theory) of 1,2-trimethylene-naphthimidazole of boiling point$_{0.05}$ 215°–220° C and melting point 191° C (on recrystallisation from 3 parts of ethyl acetate) are obtained.

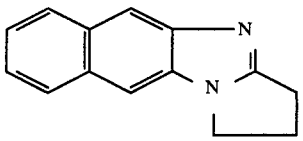

EXAMPLE 12

20 g of HCl gas are passed into a fused mixture of 84.5 g (0.5 mol) of 4-tert.-butyl-caprolactam and 119 g (0.75 mol) of 2,3-naphthylenediamine at 100° to 200° C. The mixture is then heated to 250° C under nitrogen whilst stirring and is kept at this temperature for 5 hours, in the course of which 9 g of water are distilled off through a bridge. The melt is pulverised after cooling and is shaken vigorously with a mixture of 100 g of 45% strength sodium hydroxide solution and 400 ml of water, with addition of 1,000 ml of CH$_2$Cl$_2$. The organic phase is separated off, dried over Na$_2$SO$_4$ and concentrated under reduced pressure, and on fractional distillation 85 g (58.2% of theory) of 1,2-(3'-tert.butyl-pentamethylene)-naphthimidazole of boiling point$_{0.05}$ 230°–233° C and melting point 182° C (on recrystallisation from 2 parts of butyl acetate) are obtained.

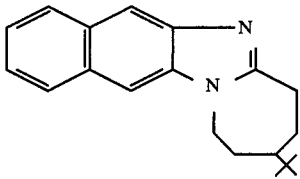

EXAMPLE 13

A mixture of 85 g (0.5 mol) of naphtholactam, 59.4 g (0.55 mol) of o-phenylenediamine and 15 g of 85% strength phosphoric acid is fused under nitrogen, whilst stirring. In the course thereof, a total of 8.5 g of water distil from the reaction mixture from 180° C. The temperature is brought to 300° C over the course of 2 hours and is kept thereat for about 4 hours longer. On subsequent fractional distillation, 91 g (75% of theory) of 1,2-naphthylene-(1',8')-benzimidazole are obtained as brownish crystals of boiling point$_{0.1}$ 232°–234° C and melting point 132° C (on recrystallisation from 3 parts of isopropanol).

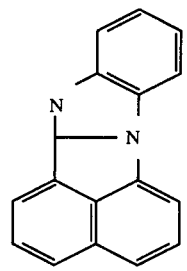

EXAMPLE 14

83 g (0.53 mol) of 1,8-naphthylenediamine, 43 g (0.5 mol) of pyrrolidone and 15 g of 85% strength H$_3$PO$_4$ are mixed, the mixture is fused whilst stirring under nitrogen and about 17 g of water, mixed with ammonia, are distilled over the course of 4 hours at a sump temperature of 150° to 285° C. The temperature is maintained at 285° C for a further 2 hours, the melt is then stirred into 500 ml of ice water, and the mixture is rendered alkaline with 50 g of 45% strength sodium hydroxide solution and extracted by shaking with 500 ml of methylene chloride. After filtering off, 75 g of dark crystals are obtained, whilst a further 30 g are obtained after concentrating the methylene chloride phase. Fractional distillation in vacuo gives 46 g (44.3% of theory) of 1,2-trimethyleneperimidine; greenish crystals of boiling point$_{0.04}$ 210°–213° C and melting point 141° C (on recrystallisation from 8 parts of ethyl acetate).

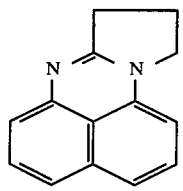

EXAMPLE 15

41 g (0.2 mol) of 2-(3'-methylaminopropyl)-5-methylbenzimidazole and 2.5 g of methanesulphonic acid are heated for 10 hours to 300°–320° C under nitrogen whilst stirring and removing methylamine gas at the head. On subsequent fractional distillation, a mixture of the two isomers 5-methyl- and 6-methyl-1,2-trimethylenebenzimidazole are obtained as a viscous oil of boiling point$_{0.2}$ 143°–145° C, which solidifies to crystals; the yield is 25 g (72.5% of theory).

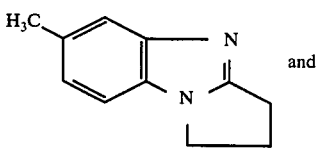

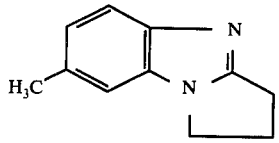

EXAMPLE 16

The same isomer mixture as in Example 15 is obtained when 64 g (0.75 mol) of pyrrolidone, 98 g (0.8 mol) of 3,4-diaminotoluene and 15 g of 85% strength phosphoric acid are gradually heated over the course of 6 hours from about 150° C to 300° C whilst stirring under nitrogen, during which time about 21 g of ammoniacal water pass over, and the mixture is kept for a further 3 to 4 hours at 300° C, until the elimination of ammonia has ceased. The reaction product is then distilled off in vacuo, a further 64 g of pyrrolidone and 98 g of 3,4-diaminotoluene are added to the distillation residue and the procedure described above is followed. On redistillation of the combined distillates from both batches, 183 g (70.9% of theory) of the same composition as in Example 8a are obtained; boiling point$_{0.3}$ 147°–148° C.

EXAMPLE 17

97.5 g (0.5 mol) of 2,3-diaminotoluene dihydrochloride are mixed with 56.5 g (0.5 mol) of caprolactam and the mixture is fused in an oil bath under nitrogen, whilst stirring. It is then heated from 180° to 275° C over the course of 2 hours, whereupon 9.5 g of aqueous distillate pass over. Thereafter the temperature is maintained at 300°–310° C for a further 6 hours, the dark melt is stirred into about 500 ml of water, the mixture is covered with 500 ml of CH$_2$Cl$_2$, about 100 g of 45% strength sodium hydroxide solution are added until the mixture reacts alkaline, and the whole is extracted by shaking. The CH$_2$Cl$_2$ phase, after drying over Na$_2$SO$_4$ and concentration under reduced pressure, gives 109 g of a viscous oil which on fractional distillation yields a mixture of the two isomeric benzimidazole 4-methyl- and 7-methyl-1,2-pentamethylenebenzimidazole; brownish viscous oil of boiling point$_{0.3}$ 154°–155° C; the yield is 72.5 g (72.5% of theory).

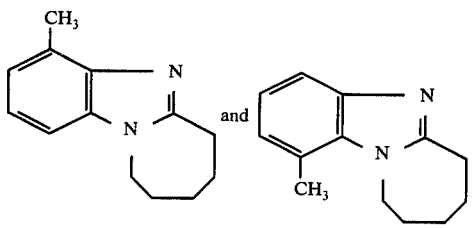

EXAMPLE 18

A mixture of 105 g (0.5 mol) of 4,5-diamino-1,3-dimethylbenzene dihydrochloride and 56.5 g (0.5 mol) of caprolactam is heated in an oil bath under nitrogen. As soon as the semi-crystalline melt becomes stirrable at about 170° C, stirring is commenced and the mixture is next kept for 5 hours at 170° to 200° C, 5 hours at 250°–300° C and 5 hours at 310° C. In the course thereof, a total of about 13 g of aqueous distillate pass over. The melt is then stirred into about 500 ml of water, the mixture is rendered alkaline with 150 g of 45% strength NaOH and the organic phase is taken up by repeated extraction by shaking with a total of about 750 ml of CH$_2$Cl$_2$. After drying over Na$_2$SO$_4$, the organic phase is concentrated under reduced pressure and the dark oil which remains (108 g) is distilled fractionally in vacuo. A mixture of the two isomers 4,6-dimethyl-1,2-pentamethylene-benzimidazole and 5,7-dimethyl-1,2-pentamethylene-benzimidazole is obtained as a yellowish-tinged brownish viscous oil of boiling point$_{0.3}$ 168°–170° C. The yield is 81.7 g (76.3% of theory).

EXAMPLE 19

11 g (0.1 mol) of 2,3-diamino-pyridine are heated with 8.5 g (0.1 mol) of pyrrolidone and 5 g of 85% strength phosphoric acid under nitrogen; water as well as ammonia are eliminated at 150° C. The temperature is raised from 150° to 250° C over the course of 6 hours, whereupon 1.9 g of aqueous distillate pass over. After cooling, the reaction mixture is treated with 150 ml of 2 N sodium hydroxide solution, the whole is extracted by shaking with about 300 ml of CH$_2$Cl$_2$ and the extract is concentrated under reduced pressure and distilled on vacuo. In this way, 8.1 g (50.9% of theory) of 1,2-trimethylene-pyrido[2,3-d]imidazole are obtained as colourless crystals of boiling point$_{0.3}$ 162°–168° C and melting point 185° C.

EXAMPLE 20

198.5 g (2 mols) of piperidone-2 and 238 g (2.2 mols) of o-phenylenediamine are fused with 30 g of 85% strength phosphoric acid whilst stirring and passing nitrogen over the mixture; from 170° C internal temperature, the elimination of water commences. The mixture is gradually heated to 320° C over the course of 5 hours and is kept at 320° C for a further 2 hours, until the evolution of NH$_3$ subsides. All volatile matter is subsequently distilled off the residue (about 60 g) in an oil pump vacuum at about 130° to 200° C/0.2 mm Hg, a further 198.5 g (2 mols) of piperidone-2 and 238 g (2.2 mols) of o-phenylenediamine are added to the distillation residue which still contains the phosphoric acid, and the procedure indicated above is again followed. This procedure is repeated twice more and the total distillate originating from four 2 mol batches is then redistilled fractionally. This gives 1,145 g (83.2% of theory) of 1,2-tetramethylene-benzimidazole of boiling point 147°–149° C/0.3 mm Hg and melting point 106° C after recrystallisation from 2 parts of ethyl acetate.

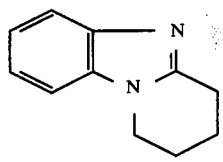

EXAMPLE 21

197 g (1 mol) of 6-cyclohexylcaprolactam, 108 g (1 mol) of o-phenylenediamine and 15 g of 85% strength $H_3PO_4$ (remainder water) are mixed and fused whilst stirring and passing nitrogen over the mixture. The elimination of water starts from 190° C. The mixture is additionally kept at 200° to 230° C for 3 hours, in the course of which about 20 g of water pass over, and the temperature is then brought to 300° C over the course of 2 hours. After a further 8 hours at 300° to 320° C, the mixture is distilled fractionally in an oil pump vacuum and 86 g (32% of theory) of 1,2-(1'-cyclohexylpentamethylene)-benzimidazole are obtained as an almost colourless viscous oil of boiling point 203° to 205° C/0.2 mm Hg.

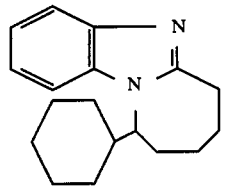

EXAMPLE 22

97.6 g (0.5 mol) of phenanthridone, 60 g (0.55 mol) of o-phenylenediamine and 15 g of 85% strength $H_3PO_4$ (remainder water) are mixed and fused under nitrogen. The elimination of $H_2O$ starts from 200° C. The temperature is gradually raised to 300° C over the course of 6 hours, whilst stirring, and is additionally kept at 300° to 330° C for 8 hours. In the course of this time, about 12 g of $H_2O$ have distilled over. A fractional distillation in an oil pump vacuum is then carried out and 77 g (57.5% of theory) of benzimidazo-[1,2-f]-phenanthridine of boiling point 227° C/0.4 mm Hg and melting point 153° C are obtained as almost colourless crystals (after recrystallisation from 5 parts of ethanol).

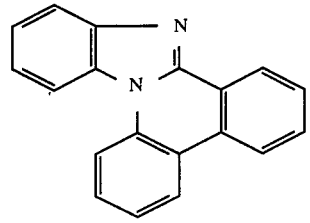

EXAMPLE 23

Test of corrosion of copper.

The test was carried out analogously to DIN 51,759.

The test sheets, namely copper sheets of size 13 × 75 × 2 mm, are polished with emery cloth of fineness 00 and then degreased with an alcohol/benzene mixture. The sheets are then dried with a linen cloth. The test sheets pretreated in this way are weighed and then covered, in a 50 cm³ measuring cylinder, with 40 ml of the solution to be examined. The measuring cylinders are then placed for three hours in a drying cabinet at 50° or 80° C.

After the test, the sheets are degreased, optically examined and weighed. The oil used is spindle oil 16, in which 1,000 ppm of flowers of sulphur were dissolved at 80° C.

The copper deactivator is added in concentrations of between 100 and 500 ppm.

Suitable inhibitors for use in practice are only those which, in addition to having a good protective action on copper, will readily dissolve in amounts of 1,000 ppm in mineral oil at up to 80° C. Furthermore, the inhibitors must be heat-stable up to 300° C.

Table 1

| | Oil tests at 50° C in spindle oil with 1,000 ppm of sulphur | | | |
|---|---|---|---|---|
| Inhibitor | Use concentration in ppm | Weight increase of the copper sheets in mg | Appearance of the copper sheets | of the solution |
| 1,2-Pentamethylene-benzimidazole | 100 | — | trace of black deposit | clear |
| | 200 | 0.50 | " | " |
| | 500 | 0.25 | almost unchanged | " |
| commercially available inhibitor | 100 | 4.2 | black deposit | " |
| | 200 | 4.0 | " | " |
| | 500 | 1.5 | trace of black deposit | " |
| without inhibitor | — | 2.0 | black deposit | " |

Table 2

| | Oil tests at 80° C in spindle oil with 1,000 ppm of sulphur | | | |
|---|---|---|---|---|
| Inhibitor | Use concentration in ppm | Weight increase of the copper sheets in mg | Appearance of the copper sheets | of the solution |
| 1,2-Trimethylene-benzimidazole | 100 | 0.5 | almost unchanged | clear |
| 1,2-Tetramethylene-benzimidazole | 100 | 1.5 | trace of black deposit | " |
| 1,2-Pentamethylene-benzimidazole | 100 | — | some black deposit | " |
| | 200 | — | trace of black deposit | " |
| | 500 | 1.0 | " | " |
| commercially available inhibitor | 100 | 8.0 | heavy black deposit | " |
| | 200 | 8.0 | " | " |
| | 500 | 3.5 | some black deposit | " |

Table 2-continued

| | Oil tests at 80° C in spindle oil with 1,000 ppm of sulphur | | | |
|---|---|---|---|---|
| Inhibitor | Use concentration in ppm | Weight increase of the copper sheets in mg | Appearance of the copper sheets | of the solution |
| without inhibitor | — | 3.0 | heavy black deposit | " |

EXAMPLE 24

Test of corrosion inhibitors in anti-freeze and anti-corrosion formulations.

The test was carried out analogously to ASTM-D-1384-70.

The following anti-corrosion packets were tested at the use concentration of 1.65% by weight in Examples a – f:

| | |
|---|---|
| sodium benzoate | 66.05% by weight |
| sodium nitrite | 6.65% by weight |
| borax | 13.8% by weight |
| sodium carbonate | 7.85% by weight |
| sodium silicate | 0.25% by weight |
| sodium nitrate | 4.9% by weight |
| benzimidazole derivative | 0.5% by weight |

The following benzimidazole derivatives were used in the following examples:

| | |
|---|---|
| Examples a and d | 1,2-pentamethylene-benzimidazole |
| Examples b and e | 1,2-trimethylene-benzimidazole |
| Examples c and f | 1,2-tetramethylene-benzimidazole |
| Example g | commercially available anti-freeze agent (consisting of 0.05% of sodium nitrite, 3.5% of borax and sodium silicate) |

Tables

Test analogous to ASTM-D-1384-70

The figures in the tables show the weight losses found, converted to g/m².

| | Example | | | |
|---|---|---|---|---|
| | a | b | c | g |
| Copper | 0.6 | 1.0 | 0.4 | 0.7 |
| Solder | 0.4 | 2.2 | 3.5 | 2.7 |
| Brass | 0.4 | 0.0 | 0.4 | 1.2 |
| Cast iron | +0.6 | 0.3 | +1.2 | 0.6 |
| Steel | +0.8 | 0.8 | 0.2 | 1.0 |
| Silumin | 0.1 | 7.8 | 1.1 | 1.5 |

Optical examination shows a grey to black continuous layer, formed by passivation, when using the products according to a to f. In comparison example g, crevice corrosion, pitting or graining is observed.

Medium: corrosive water according to ASTM-D-1384-70 without glycol constituent.

The figures in the table show the weight losses found, converted to g/m².

| | Example | | |
|---|---|---|---|
| | d | e | f |
| Copper | 1.0 | 0.0 | 0.2 |
| Solder | 1.1 | 2.0 | 2.2 |
| Brass | +1.6 | 0.4 | 0.8 |
| Cast iron | 5.7 | +0.2 | +0.8 |
| Steel | +2.6 | +0.6 | +0.4 |
| Silumin | 0.0 | 4.8 | 6.3 |

What is claimed is:

1. Method for protecting metal from erosion comprising treating the metal with a compound having the formula

wherein

A is an arylene radical and

B is unsubstituted or halogen, lower alkyl, $CF_3$, alkoxy, aryloxy or dialkylamino substituted alkylene chain

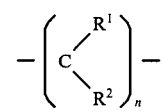

wherein $R^1$ and $R^2$ individually represent hydrogen and/or unsubstituted or halogen, lower alkyl, $CF_3$, alkoxy, aryloxy or dialkylamino substituted aliphatic, cycloaliphatic, araliphatic or aromatic radicals and $n$ represents a number from 3 to 6, or B is unsubstituted or a halogen, lower alkyl, $CF_3$, alkoxy, aryloxy or dialkylamino substituted 1,8-naphthylene, 2,2'-diohenylene or 4,5-phenanthrylene radical.

2. Method of claim 1 wherein A is a naphthylene, phenylene, or diphenylene radical, $R^1$ and $R^2$ are, individually, hydrogen, a straight or branched chain aliphatic radical containing up to 8 carbon atoms, an araliphatic radical containing from 7 to 12 carbon atoms, unsubstituted or a halogen, lower alkyl, $CF_3$, alkoxy, aryloxy or dialkylamino substituted naphthyl- or phenyl radical and $R^3$ and $R^4$ are, individually, hydrogen, a straight or branched chain aliphatic radical containing up to 12 carbon atoms, a cycloaliphatic radical containing up to 8 carbon atoms, or an araliphatic radical containing from 7 to 12 carbon atoms.

3. Method of claim 1 wherein A is a 2,3- or 3,4-pyridylene radical, a 1,2-,2,3- or 1,8-naphthylene radical or a 1,2-phenylene radical each optionally substituted by an alkyl group containing from 1 to 6 carbon atoms, $R^1$ and $R^2$ independently represent hydrogen, an alkyl radical containing up to 6 carbon atoms, a cyclopentyl radical, a cyclohexyl radical, a benzyl radical or a phenyl radical, and $n$ is an integer of from 3 to 6.

4. Method of claim 1 wherein

A is phenylene, naphthylene, optimally substituted by lower alkyl and halogen B is

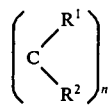

$R^1$ and $R^2$ are each hydrogen or lower alkyl, and $n$ is 3 to 5.

5. Method of claim 1 wherein the compound is one of the formula

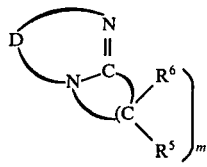

in which

D denotes a 2,3- or 3,4-pyridylene radical, a 1,2-, 2,3- or 1,8-naphthylene radical or 1,2-phenylene radical, these radicals being optionally substituted, preferably by alkyl with up to 6 C atoms, $R^5$ and $R^6$ represent hydrogen or alkyl with up to 6 carbon atoms, cyclopentyl, cyclohexyl, benzyl or phenyl, and $m$ denotes one of the numbers 3, 4, 5 or 6, the $m$ radicals $R^5$ and $R^6$ optionally being different.

6. Method of claim 1 wherein the compound is one of the formula

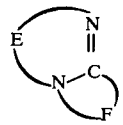

wherein

E denotes a substituted or unsubstituted radical selected from the group of 1,2-phenylene, 1,2-naphthylene and 2,3-pyridylene, and F denotes a substituted to unaubstituted radical selected from the group of trimethylene, pentamethylene, 2,2-diphenylene and 1,8-naphthylene.

7. Method of claim 1 wherein the compound is one of the formula

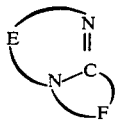

wherein

E denotes a substituted or unsubstituted radical selected from the group of 1,2-phenylene, 1,2-naphthylene and 2,3-pyridylene, and F denotes a substituted or unsubstituted radical selected from the group of trimethylene, pentamethylene, 2,2'-diphenylene and 1,8-naphthylene.

8. Method of claim 1 wherein the compound is one of the group consisting of 1,2-(3'-tert.-butyl-pentamethylene)-benzimidazole;
1,2-(3'-tert.-butyl-pentamethylene)-naphthimidazole;
1,2-naphthylene-(1',8')-benzimidazole;
4,6-dimethyl-1,2-pentamethylene-benzimidazole;
5,7-dimethyl-1,2-pentamethylene-benzimidazole;
1,2-trimethylene-pyrido-[2,3-d]-imidazole;
1,2-(1'-cyclohexylpentamethylene)-benzimidazole; and
benzimidazo-[1,2-f]phenanthridine.

* * * * *